US006699465B2

(12) United States Patent
Scott

(10) Patent No.: US 6,699,465 B2
(45) Date of Patent: Mar. 2, 2004

(54) COVALENT ATTACHMENT OF POLYMER TO CELL TO PREVENT VIRUS BONDING TO RECEPTOR

(75) Inventor: Mark D. Scott, Clifton Park, NY (US)

(73) Assignee: Albany Medical College, Albany, NY (US)

( * ) Notice: Subject to any disclaimer, the term of this patent is extended or adjusted under 35 U.S.C. 154(b) by 179 days.

(21) Appl. No.: 09/861,491

(22) Filed: May 18, 2001

(65) Prior Publication Data

US 2002/0173029 A1 Nov. 21, 2002

(51) Int. Cl.$^7$ .......................... A61K 31/74; C12N 1/08; C12N 7/00; C12N 5/06; C12N 5/08

(52) U.S. Cl. .................. 424/78.08; 424/93.7; 435/177; 435/178; 435/180; 435/235.1; 435/325; 435/371

(58) Field of Search ............................ 424/78.08, 93.1, 424/93.7, 486; 435/174, 177, 178, 180, 235.1, 325, 371

(56) References Cited

U.S. PATENT DOCUMENTS

| | | | |
|---|---|---|---|
| 4,020,183 A | 4/1977 | Asculai et al. | 424/341 |
| 4,139,630 A | 2/1979 | Asculai et al. | 424/283 |
| 4,147,803 A | 4/1979 | Asculai et al. | 424/320 |
| 4,507,281 A | 3/1985 | Asculai et al. | 424/85 |
| 4,591,505 A | 5/1986 | Prince | 424/101 |
| 4,897,304 A | 1/1990 | Hossain et al. | 424/289 |
| 4,957,734 A | 9/1990 | Miller | 424/85.7 |
| 5,182,104 A | 1/1993 | Marcus et al. | 424/78.07 |
| 5,663,161 A | 9/1997 | Bell | 514/183 |
| 5,671,754 A | 9/1997 | Schmukler et al. | 128/824 |
| 5,770,199 A | 6/1998 | Eibl et al. | 424/176.1 |
| 5,952,392 A | 9/1999 | Katz et al. | 514/724 |

OTHER PUBLICATIONS

Selma Mizouni, Viral Modification with Methoxypoly(Ethylene Glycol): Implication for Viral Inactivation and Gene Therapy?, Thesis, Jun. 8, 2000, pp. 1–59.

Mizouni et al., Viral Modification with Methoxypoly(Ethylene Glycol): Implications for Gene Therapy and Viral Inactivation, 1998, Blood 92 (Suppl. 1), 4627, 1 page.

Mizouni et al., Use of a Two–Phase Partitioning System to Purify an Immunologically Attenuated Viral Vector, 1999, Blood 94 (Suppl. 1) 5081 (415b), 1 page.

*Primary Examiner*—David M. Naff

(74) *Attorney, Agent, or Firm*—Schmeiser, Olsen & Watts

(57) ABSTRACT

A chemo-physiological structure and method for forming the chemo-physiological structure. In a first embodiment, a cell of an animal is provided. The cell has a membrane surface and a viral receptor coupled to the membrane surface. A linker molecule having a covalently attached polymer is covalently bonded to the membrane surface, the viral receptor, or both. The polymer prevents an extracellular virus from bonding to the viral receptor. In a second embodiment, a linker molecule having a covalently attached polymer is covalently bonded to a capsid of a virus, which prevents the virus from bonding to a viral receptor of an adjacent or nearby animal cell.

125 Claims, 10 Drawing Sheets

EXAMPLES OF VIRUSES OF HUMAN OR VETERINARY IMPORTANCE

| VIRUS | VIRAL FAMILY | HUMAN SIGNIFICANCE | VETERINARY SIGNIFICANCE |
|---|---|---|---|
| Simian Vaculating Virus 40 (SV40) | Polyomaviridae | | + |
| Influenza A/B Viruses | Orthomyxoviridae | + | + |
| Epstein-Barr Virus | Herpesviridae | + | + |
| Rhinoviruses (multiple) | Picornaviridae | + | + |
| Rotaviruses (multiple) | Reoviridae | + | + |
| Respiratory Syncytial Virus | Paramyxoviridae | + | + |
| Adenoviruses (multiple) | Andoviridae | + | + |
| Coxsackievirus (multiple) | Picornaviridae | + | + |
| Coronavirus (multiple) | Coronaviridae | + | + |
| Parainfluenza Virus (multiple) | Paramyxoviridae | + | + |
| Mumps Virus | Paramyxoviridae | + | |
| Hepatitis A Virus | Picornaviridae | + | + |
| Hepatitis B Virus | Hepadnaviridae | + | + |
| Hepatitis C Virus | Flaviviridae | + | + |
| Hepatitis D Virus | 'Viroid-Like' | + | + |
| Hepatitis E Virus | 'Norwalk–Like' | + | + |
| Variola Virus | Poxviridae | + | + |
| Hanta Virus | Hantavirus | + | + |
| Dengue Virus 1-4 | Togaviridae | + | |
| Measles Virus | Paramyxoviridae | + | |
| Rubella Virus | Togaviridae | + | |
| Parvovirus | Parvoviridae | + | |
| Herpes Simplex Virus 1, 2 | Herpesviridae | + | |
| HTLV-I | Retroviridae | + | |
| HTLV-II | Retroviridae | + | |
| Human Immunodeficiency Virus (HIV-1, HIV-2) | Retroviridae | + | |
| Simian Immunodeficiency Virus (SIV) | Retroviridae | | + |
| Papillomavirus | Papovaviridae | + | |
| Poliovirus | Picornaviridae | + | |
| Rabies Virus | Rhabdoviridae | + | + |
| Various Encephalitis Viruses (e.g., Tick-borne, Mosquito-borne; Human, Equine, etc.) | Togaviridae Flaviviridae Bunyaviridae | + | + |
| Feline Leukemia Virus | Parvoviridae | | + |
| Feline Immunodeficiency Virus | Retroviridae | | + |
| Canine Parvovirus | Parvoviridae | | + |
| Canine Distemper Virus | Paramyxoviridae | | + |
| Mucosal Disease Virus (Cattle) | Togaviridae | | + |
| Rift Valley Fever | Bunyaviridae Togaviridae | + | + |
| African Swine Fever Virus | Iridoviridae | | + |
| Marburg Viruses | Filoviridae | + | + |
| Hemorrhagic Viruses (multiple) | Flaviviridae Arenaviridae Bunyaviridae | + | + |

*FIG. 5*

EXAMPLES OF PEG LINKER CHEMISTRY CAPABLE OF CELLULAR AND VIRAL SURFACE MODIFICATION

| NAME OF POLYMERATED LINKER CHEMICAL (PLC) | TARGET OF PLC |
|---|---|
| aldehyde PEG | Reacts with Primary Amines |
| w-amino-a-carboxyl PEG | Protein Amino Groups |
| benzotriazole carbonate | Protein Amino Groups (primarily lysine) |
| carbonylimidazole PEG | Protein Amino Groups |
| cynauric chloride PEG | Protein Amino Groups (primarily lysine) |
| epoxide PEG | Amino, Hydroxyl, and Thiol groups |
| glycidyl ether (epoxide) of PEG | Amino, Hydroxyl, and Thiol groups |
| isocyanate PEG | Alcohol Groups and Amines |
| maleimide PEG | Thiol Groups |
| N-hydroxysuccinimidyl-maleimide (NHS-maleimide) | Amine and Thiol Groups |
| NHS-vinylsulfone | Amine and Thiol Groups |
| NHS-PEG2 | Amine and Thiol Groups |
| p-nitrophenylcarbonate PEG | Protein Amino Groups |
| oxycarbonylimidazole PEG | Amine Groups |
| orthopyridyl disulfide | Thiol Groups |
| phospholipid PEG | Intercalates into Lipid Membrane/Capsid Surfaces (no covalent bonding) |
| succinimidyl butanoate (SBA-PEG) | Lysine and Terminal Amines |
| succinimidyl ester of carboxymethylated PEG | Lysine and Terminal Amines |
| succinimidyl propionate (SPA-PEG) | Lysine and Terminal Amines |
| succinimidyl succinamide (SSA-PEG) | Lysine and Terminal Amines |
| succinimidyl succinate PEG (SS-PEG) | Amine Groups |
| thiol PEG | Thiol Groups |

*FIG. 7*

COVALENT ATTACHMENT OF POLYMER TO CELL TO PREVENT VIRUS BONDING TO RECEPTOR

BACKGROUND OF THE INVENTION

1. Technical Field

The present invention relates generally to covalent modification of surface protein or carbohydrate for protecting an animal against viral attack.

2. Related Art

FIG. 1 illustrates a cellular cross-sectional view of viral disease pathogenesis, in accordance with the related art. FIG. 1 shows cells 10 and 20 within an extracelluar environment 15. The cell 10 comprises a cell interior 12, and a nucleus 11 within the cell interior 12. A viral receptor 14 is coupled to a membrane surface 13 of the cell 10. The cell 20 comprises a cell interior 22 and a nucleus 21 within the cell interior 22. A viral receptor 24 is coupled to a membrane surface 23 of the cell 20.

An extracellular virus 1 in the extracellular environment 15 enters the cell 10 through the viral receptor 14. While within the cell interior 12 of the cell 10, the virus 1 undergoes multiple rounds of replication, resulting in the replication of viral DNA, RNA, and protein from viruses 2, 3, 4, and 5, which: are packaged into their envelopes to become viruses 6, 7, 8, and 9, respectively; and pass through the membrane surface 13 into the extracellular environment 15.

The virus 9 enters the cell 20 through the viral receptor 24. While within the cell interior 22 of the cell 20, the virus 9 undergoes multiple rounds of replication (not shown) in the cell interior 22 of the cell 20, and subsequently passes through the membrane surface 23 enters the extracellular environment 15 as replicated viruses 27, 28, and 29.

Unfortunately, the viral replication in the cells 10 and 20, as described supra, causes destruction of the cells 10 and 20 and possible consequent viral disease of an animal (i.e., a human or non-human animal) that comprises the cells 10 and 20. Thus, there is a need to prevent such viral disease from occurring in the animal.

SUMMARY OF THE INVENTION

The present invention provides a chemo-physiological structure, comprising:
 a membrane surface of a cell of an animal;
 a viral receptor coupled to the membrane surface; and
 a linker molecule covalently bonded to a tissue member selected from the group consisting of the membrane surface, the viral receptor, and a combination thereof, wherein a polymer is covalently attached to the linker molecule, and wherein the polymer prevents an extracellular virus from bonding to the viral receptor.

The present invention provides a method for forming a chemo-physiological structure, comprising:
 providing a membrane surface of a cell of an animal and a viral receptor coupled to the membrane surface; and
 covalently bonding a linker molecule to a tissue member selected from the group consisting of the membrane surface, the viral receptor, and a combination thereof, wherein a polymer is covalently attached to the linker molecule, and wherein the polymer prevents an extracellular virus from bonding to the viral receptor.

The present invention provides a chemo-physiological structure, comprising:
 a virus having a capsid; and
 a linker molecule covalently bonded to the capsid, wherein a polymer is covalently attached to the linker molecule, and wherein the polymer envelops the virus in a manner that prevents the virus from bonding to a cell of an animal.

The present invention provides a method for forming a chemo-physiological structure, comprising:
 providing a virus having a capsid; and
 covalently bonding a linker molecule to the capsid, wherein a polymer is covalently attached to the linker molecule, and wherein the polymer envelops the virus in a manner that prevents the virus from bonding to a cell of an animal.

The present invention prevents a virus from recognizing the viral receptors or the cell membrane of an animal cell, and thus from entering an interior portion of the cell. Accordingly, the present invention protects the animal cell against viral attack and prevents viral infection of the animal. The present invention may be used to prevent viral infection in both human animals and non-human animals.

BRIEF DESCRIPTION OF THE DRAWINGS

FIG. 5 lists exemplary viruses of human significance and of veterinary significance, in accordance with embodiments of the present invention.

FIG. 7 lists exemplary polymeric linker compounds and associated protein or carbohydrate targets that can be covalently reacted with the exemplary polymeric linker compounds, for use in conjunction with FIG. 2 and in accordance with embodiments of the present invention.

DETAILED DESCRIPTION OF THE INVENTION

Figure 1:
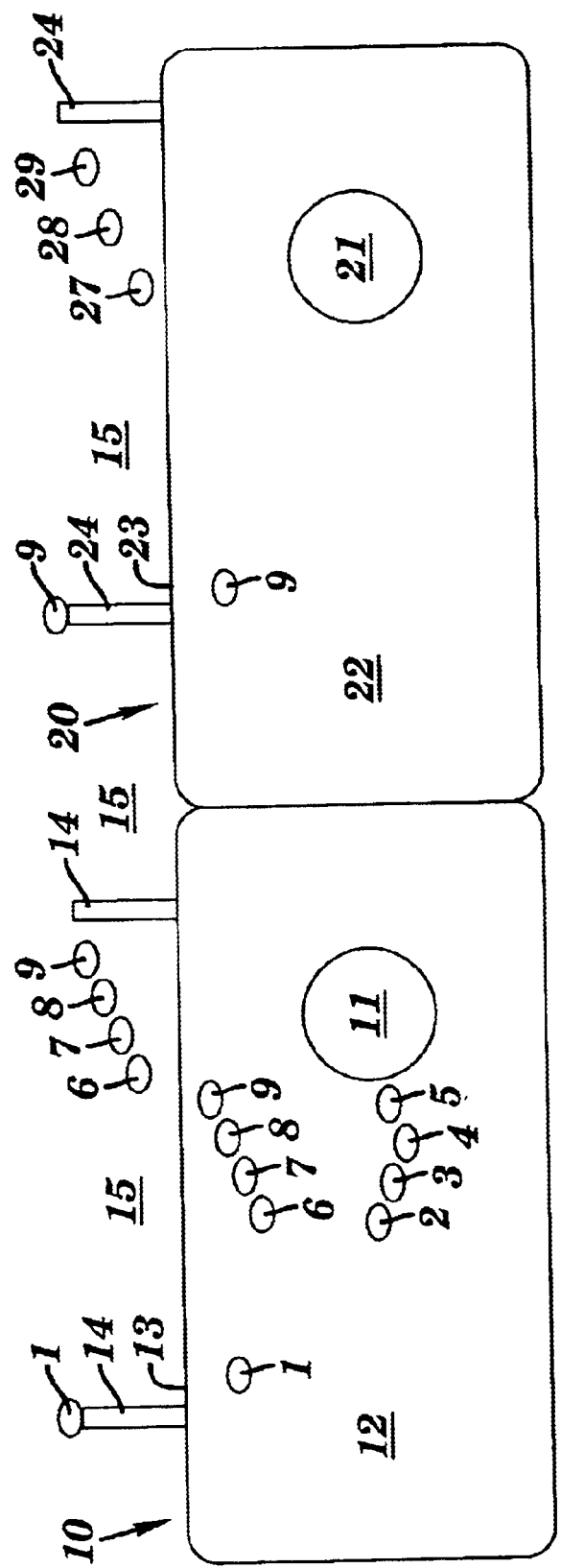
FIG. 1 depicts a cellular cross-sectional view of viral disease pathogenesis, in accordance with the related art.
Figure 2:
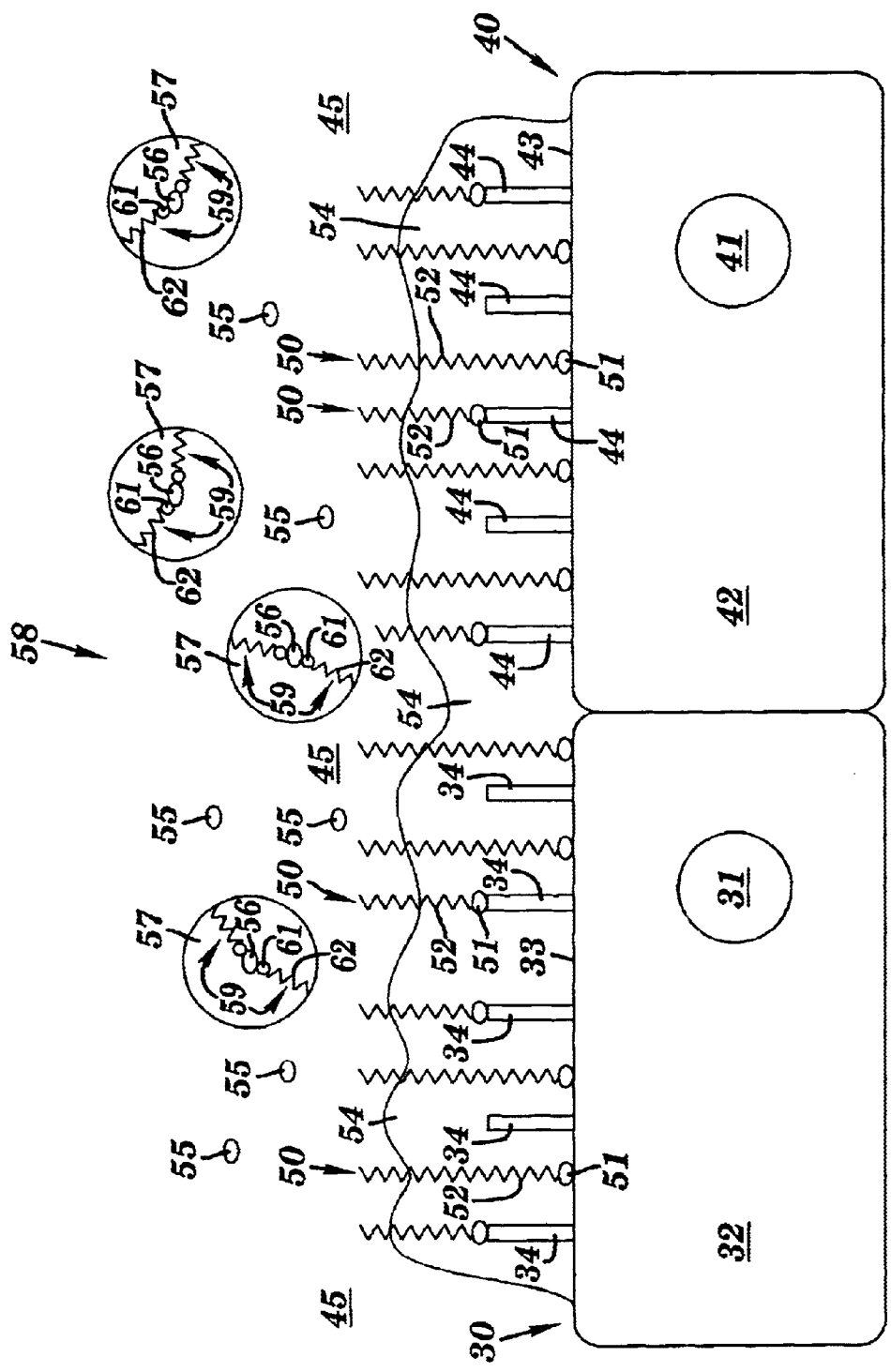
FIG. 2 depicts a cellular cross-sectional view of how viral disease may be prevented by using polymerated linker chemicals, in accordance with the present invention.

FIG. 2 illustrates a cellular cross-sectional view of how viral disease may be prevented, in accordance with the present invention. FIG. 2 shows cells 30 and 40 within an extracelluar environment 45. The cell 30 comprises a cell interior 32, and a nucleus 31 within the cell interior 32. A viral receptor 34 is coupled to a membrane surface 33 of the cell 30. The cell 40 comprises a cell interior 42, and a nucleus 41 within the cell interior 42. A viral receptor 44 is coupled to a membrane surface 43 of the cell 40.

Also shown in FIG. 2 are extracellular viruses 55 and 56, which are unable to access the viral receptors 34 and 44 because of a blocker layer 54 and blocker envelopes 57 which are formed in accordance with the present invention. By being so prevented from accessing the viral receptors 34 and 44, the extracellular viruses 55 and 56 are said to be "inactivated." The blocker layer 54 results from covalent bonding of a polymerated linker chemical 50 to the viral receptors 34 and the membrane surface 33 of the cell 30, and also to the viral receptors 44 and the membrane surface 43 of the cell 40. The polymerated linker chemical 50 includes a linker molecule 51 with a covalently attached polymer 52. The polymerated linker chemical 50 is said to represent an activated form of the polymer 52 (e.g., if the polymer is methylpolyethylene glycol (mPEG), then then "activated mPEG" is exemplified by having mPEG covalently bonded to the linker molecule of cyanuric chloride). The linker molecule 51 is covalently bonded to proteins or carbohydrates in the viral receptors 34 and 44, and to proteins or carbohydrates in the membrane surfaces 33 and 43. The covalent linking of the linker molecule 51 to a protein may include a covalent linking of the linker molecule 51 to an amino acid in the protein or to a sulfhydryl group in the protein. Thus, the linker molecule 51, together with the covalently attached polymer 52, is disposed between the virus 55 (or 56) and the viral receptors 34 and 44. The polymer 52 has a "long chain length;" i.e., a chain length that is of sufficient magnitude to fill the space around itself to create the blocker layer 54. Thus, the blocker layer 54 constitutes a barrier that prevents the viruses 55 and 56 from having access to the viral receptors 34 and 44. In addition, the polymer 52 within the blocker layer 54 prevents the approach and binding of viruses by steric hindrance. Additionally, the polymer 52 may be highly hydrophillic so as to create a hydration zone around itself to alternatively create the blocker layer 54. Inasmuch as the viruses 55 and 56 would covalently bond to the viral receptors 34 and 44 via a charge-charge coupling mechanism, the hydration zone encompassed by the blocker layer 54 effectively camouflages molecular charge sites and thus prevents the viruses 55 and 56 from having access to the viral receptors 34 and 44. Thus, the polymer 52 effectively prevents the viruses 55 and 56 from recognizing the viral receptors 34 and 44 and thus from entering an interior portion of the cell 30 and of the cell 40.

The blocker envelope 57 results from covalent bonding of a polymerated linker chemical 59 with the virus 56. The polymerated linker chemical 59 includes a linker molecule 61 with a covalently attached polymer 62. The polymerated linker chemical 59 may be the same as (i.e., chemically identical to), or different from, the polymerated linker chemical 50. The linker molecule 61 is covalently bonded to proteins or carbohydrates in an outer portion (i.e., the capsid) of the virus 56. The polymer 62 has a "long chain length;" i.e., a chain length that is of sufficient magnitude to fill the space around itself to create the blocker envelope 57. Thus, the blocker envelope 57 constitutes a barrier that prevents the virus 56 from having access to the viral receptors 34 and 44 even if the blocker layer 54 were absent. In addition, the polymer 52 within the blocker layer 54 prevents, by steric hindrance, the virus 56 from approaching, and binding to, animal cells. Additionally, the polymer 62 may be highly hydrophillic so as to create a hydration zone around itself to alternatively create the blocker envelope 57. Inasmuch as the virus 56 would covalently bond to the viral receptors 34 and 44 via a charge-charge coupling mechanism, the hydration zone encompassed by the blocker envelope 57 effectively camouflages molecular charge sites and thus prevents the virus 56 from having access to the viral receptors 34 and 44 even if the blocker layer 54 were absent. Thus, the polymer 62 effectively prevents the virus 56 from recognizing the viral receptors 34 and 44 and thus from entering an interior portion of the cell 30 and of the cell 40.

Figure 3:
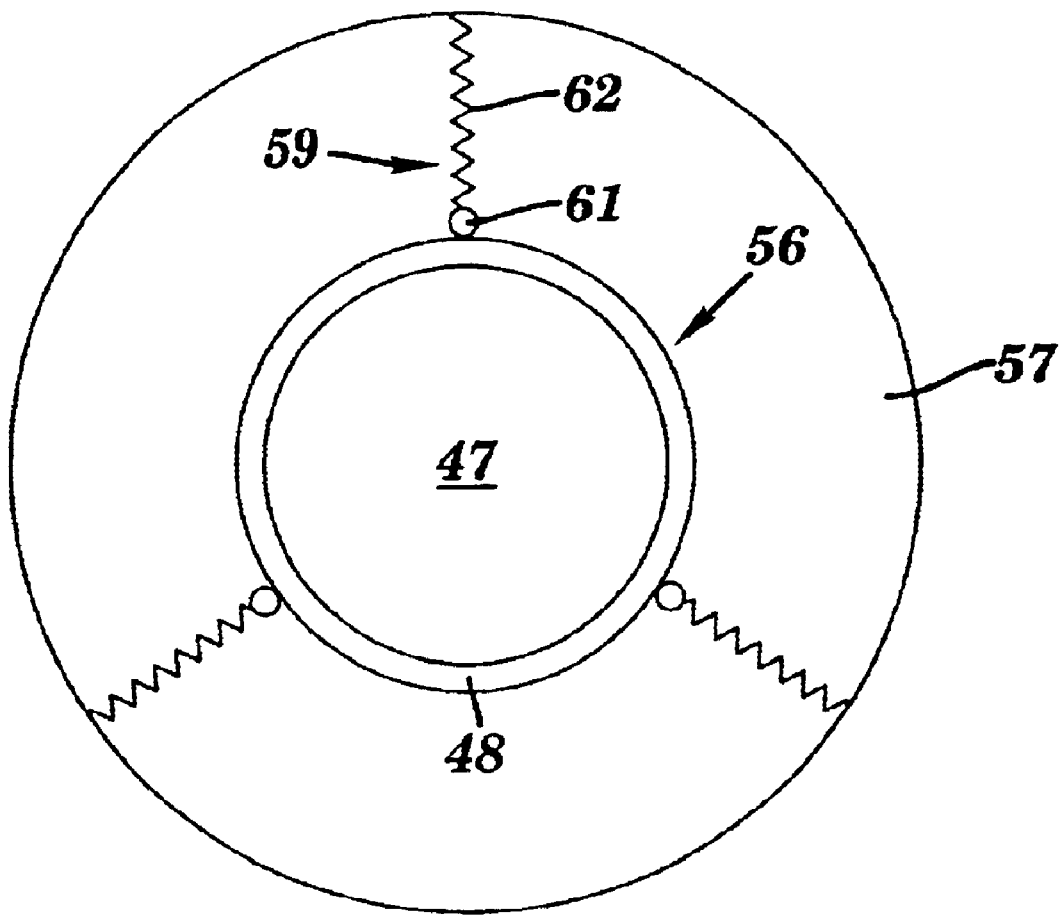
FIG. 3 is enlarged view of a virus of FIG. 2 and its surrounding environment, in accordance with embodiments of the present invention.

FIG. 3 is enlarged view of the virus 56 and blocker envelope 57 of FIG. 2, in accordance with embodiments of the present invention. The virus 56 includes a viral core 47 and a capsid 48. The viral core 47 includes genetic material (i.e., DNA or RNA). The capsid 48 is a shell comprising protein. Some viruses additionally include an outer lipid envelope (not shown) that surrounds the capsid. FIG. 3 shows that the linker molecule 61 of the polymerated linker chemical 59 is covalently bonded to the capsid 48. In particular, the polymerated linker chemical 59 may be covalently bonded to an amino acid (e.g., lysine), a sulfhydryl group, or a carbohydrate at the capsid 48. The polymer 62 of the polymerated linker chemical 59 envelops the virus 56 in a manner that prevents the virus 56 from bonding to a cell (and from entering the cell) of an animal.

Figure 4:
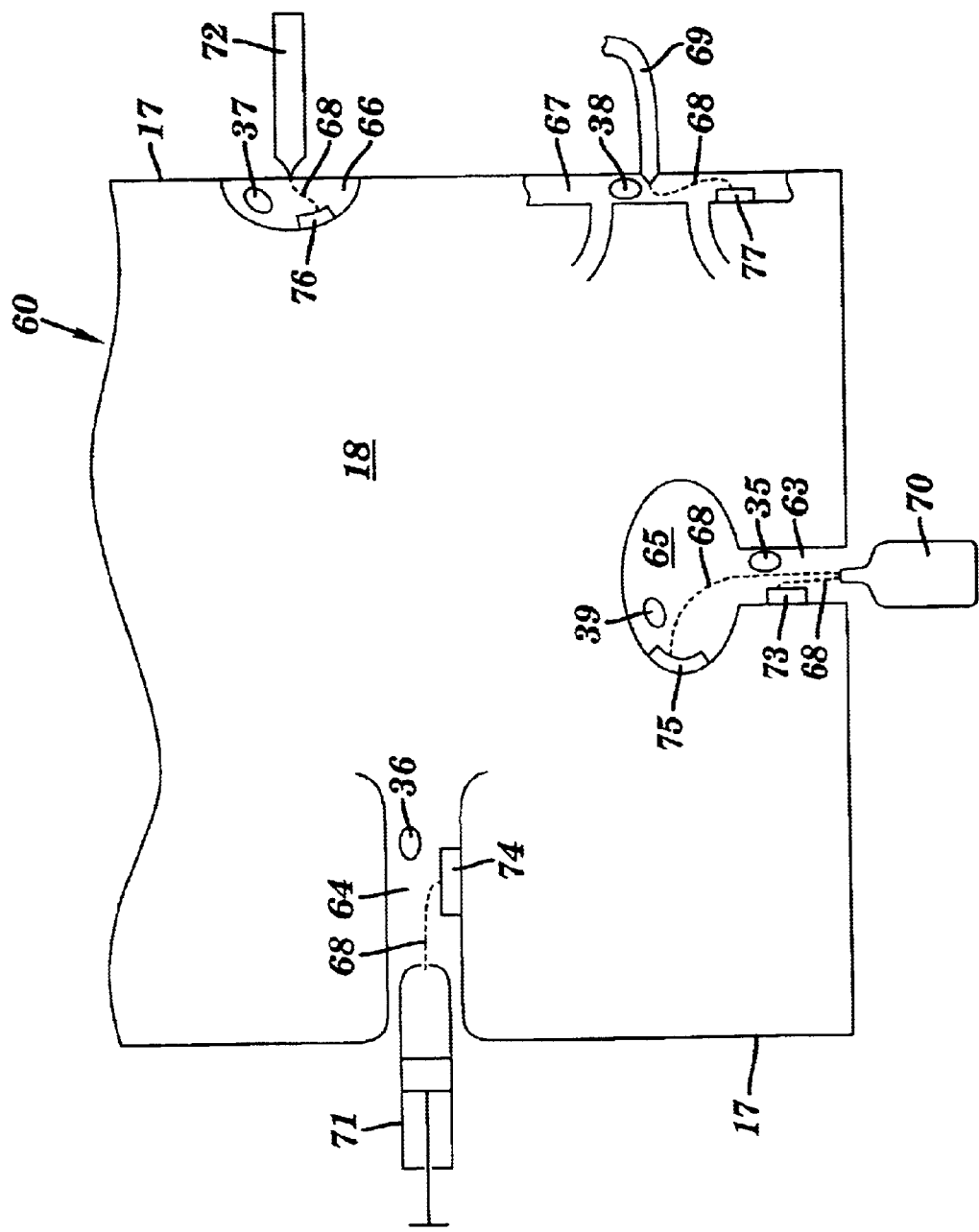
FIG. 4 depicts an animal and modes of delivering a polymerated linker chemical therein, in accordance with embodiments of the present invention.

The cells 30 and 40 of FIG. 2 may be treated in vivo within an animal 60 (see FIG. 4) with the polymerated linker chemical 50 or 59 (or both) for clinical purposes such for preventing or treating a viral infection. FIG. 4 shows the animal 60 having an epithelium 17 (i.e., membranous cellular tissue at external surfaces of the animal 60 or "skin"), an interior 18, openings 63 and 64, an organ 65 coupled to the opening 63, a muscle 66, and a blood vessel 67. The animal 60 may be a human animal (e.g., a human being or a fetus) or a veterinary animal. A veterinary animal is a non-human animal of any kind such as, inter alia, a domestic animal (e.g., dog, cat, etc.), a farm animal (cow, sheep, pig, etc.), a wild animal (e.g., a deer, fox, etc.), a laboratory animal (e.g., mouse, rat, monkey, etc.), an aquatic animal (e.g., a fish, turtle, etc.), etc. The openings 63 and 64 include a cell 73 and 74, respectively, the organ 65 includes a cell 75, the muscle 66 includes a cell 76, and the blood vessel 67 includes a cell 77. The blood vessel 67 is part of a systemic vascular system (not shown) capable of transporting polymerated linker chemical 50 or 59 (or both) to cells distributed throughout the animal 60. The openings 63 and 64 include any opening that pertains to the animal 60. If the animal 60 is a human being, for example, then the openings 63 and 64 may include, inter alia, a nasal cavity, a mouth, a vagina if the animal 60 is female, etc. The organ 65 includes any organ that pertains to the animal 60. If the animal 60 is a human being, for example, then the organ 65 may include, inter alia, a lung, a stomach, a kidney, a liver, etc. The organ 65 may be coupled to the opening 63 or 64, or may rather be coupled to the blood vessel 67 through the systemic vascular system of the animal 60. FIG. 4 also shows viruses 35, 36, 37, 38, and 39 in the opening 63, the opening 64, the muscle 66, the blood vessel 67, and the organ 65, respectively.

A polymerated linker chemical (PLC) 68 may be delivered to any cell of the animal 60 where viral infection is possible such as, inter alia, to any of the cells 73–77, or to extracellular viruses in any opening (e.g., the openings 63 and 64), in any organ (e.g., the organ 65), in any muscle (e.g., the muscle 66), in any blood vessel (e.g., the blood vessel 67), or in any other relevant location such as a peritoneal cavity, etc. Said delivery of the PLC 68 may be accomplished in any manner known to one of ordinary skill in the art such as, inter alia, via spray bottle 70 into the opening 63, via syringe 71 into the opening 64, via needle 72 into the muscle 66, and via intravenous delivery apparatus 69 into the blood vessel 67. A spray of the PLC 68 from the spray bottle 70 may be, inter alia, aerosol activated.

There are numerous examples of how the PLC 68 may be delivered to cells of the animal 60 or to viruses within the animal 60. As a first example, the PLC 68 may be packaged within the spray bottle 70 and sprayed into a nasal cavity as represented by the opening 63, where the PLC 68 generates a blocker layer (see, e.g., the blocker layer 54 of FIG. 2) on the nasal epithelial cell 73 in the nasal cavity 63, and a blocker envelope (see, e.g., the blocker envelope 57 of FIG. 2) over any extracellular virus that is present in the nasal cavity 63. The PLC 68 from the spray bottle 70, after being sprayed into the nasal cavity represented by the opening 63, may be inhaled into a lung as represented by the organ 65, where the PLC 68 generates a blocker layer on the pulmonary cell 75 in the lung, and a blocker envelope over any extracellular virus that is present in the lung. As a second example, the PLC 68 in the spray bottle 70 may be sprayed into a mouth as represented by the opening 63, and may be inhaled into a lung as represented by the organ 65, where the PLC 68 generates a blocker layer on the cell 75 in the lung, and a blocker envelope over any extracellular virus that is present in the lung. As a third example, the PLC 68 in the syringe 71 may be delivered to a vagina as by the opening 64, where the PLC 68 generates a blocker layer on the vaginal cell 74 in the vagina, and a blocker envelope over any extracellular virus that is present in the vagina. Any mechanism discussed supra in conjunction with FIG. 2 for inactivating any of the viruses in FIG. 2 may be utilized for inactivating any of the viruses in FIG. 4.

The cells 30 and 40 of FIG. 2 may be alternatively removed from the animal 60 of FIG. 4 and treated in vitro (i.e., outside of the animal) with the PLC 50 or 59, or both (see FIG. 2), such as in a laboratory setting for such purposes as, inter alia, research or testing. The PLC 50 or 59, or both may be delivered in vitro to any cell of the animal 60 that has been so removed from any portion of the animal 60, such as to, inter alia, any of the cells 73–77 of FIG. 4, in any manner known to one of ordinary skill in the art such as, inter alia, by spraying the PLC 50 or 59, or both on the cells, or by immersion of the cells into a liquid that includes the PLC 50 or 59, or both, to form a blocker layer on the cells. In addition, the PLC 50 or 59, or both, may be delivered in vitro to viruses in the vicinity of the cells so removed from the animal 60 of FIG. 4, in any manner known to one of ordinary skill in the art such as, inter alia, by spraying the PLC 50 or 59, or both, on or near the viruses to form blocker envelopes around the viruses.

FIGS. 2, 3, and 4 show "chemo-physiological structures." A chemo-physiological structure is defined herein as an organic structure that includes at least one organism (e.g., an animal, a cell, a virus, or any portion thereof) and any chemical that is covalently bonded to any organism of the at least one organism.

As discussed supra in conjunction with FIGS. 2 and 3, the present invention uses a polymerated linker chemical 50 or 59 to generate the blocker layer 54 and the blocker envelope 57, respectively, to inactivate the extracellular viruses 55 and 56 by preventing the extracellular viruses 55 and 56 from bonding with viral receptors 33 and 44 which are coupled to cells 30 and 40, respectively. The use of the blocker layer 54 and the blocker envelope 57 is non-specific as to the type of virus that is inactivated and any virus that can infect an animal (human or non-human) can be inactivated in accordance with the present invention. FIG. 5 tabulates examples of viruses that can be inactivated in accordance with the present invention. Each listed virus in FIG. 5 is classified as to whether said listed virus is of human significance or of veterinary significance. A virus is of human significance if the virus is known to one of ordinary skill in the art as being capable of infecting a human animal. A virus is of veterinary significance if the virus known to one of ordinary skill in the art as being capable of infecting a non-human animal. The list of viruses in FIG. 5 is merely exemplary. Numerous viruses other than those listed in FIG. 5 can be inactivated in accordance with the present invention.

FIG. 6 illustrates an exemplary chemistry of coupling the polymerated linker chemical, as depicted in FIG. 2 or FIG. 3, to a protein, in accordance with embodiments of the present invention. In FIG. 6, two chemical reactions are illustrated. In the first chemical reaction shown in FIG. 6, a polymer 80 reacts with a linker molecule 81 to form a polymeric linker chemical (PLC) 82 in which the polymer 80 is covalently bonded to the linker molecule 81. Specifically in FIG. 6, the polymer 80 is methoxypolyethylene glycol (mPEG) having the chemical structure of $CH_3(—O—CH_2—CH_2)_n—OH$ wherein $n \geqq 2$. The linker molecule 81 is an alkyl halide (namely, cyanuric acid) and the resultant PLC 82 is 2-O-mPEG-4,6-dichloro-s-triazine. In the first chemical reaction, the hydroxyl group ($OH^-$) is a nucleophile that reacts generally with an alkyl halide (specifically, cyanuric chloride), resulting in displacement and release of the chlorine ion ($CL^-$) in position 2 of the cyanuric chloride triazine ring as well as release of the hydrogen ion ($H^-$) from the hydroxy group of the mPEG. The first chemical reaction may be implemented in any manner known to one of ordinary skill in the art such as in, inter alia, anhydrous benzene at a temperature of about 25° C. Formation of the PLC 82 of 2-O-mPEG-4,6-dichloro-s-triazine is well-known in the art and may be obtained commercially.

In the second chemical reaction shown in FIG. 6, a protein 83 reacts with the PLC 82 to form a protein-polymer complex 84. Specifically in FIG. 6, the protein 83 includes lysine, wherein $H_3N^+—(CH_2)_4$ is a portion of the lysine that reacts with the PLC 82, and wherein X represents a remaining portion of the protein 83 including a remaining portion of the lysine. The remaining portion of the lysine has a carbon atom covalently bonded to H, $H_3N^+$, and a carboxyl group. As shown in FIG. 6, a hydrolysis of the chlorine in position 4 of the cyanuric chloride triazine ring has replaced said chlorine in position 4 with the $H_3N^+—(CH_2)_4$ portion of the lysine of the protein 83, to form the protein-polymer complex 84. Specifically in FIG. 6, the protein-polymer complex 84 is 2-O-mPEG-4-Y-6-chloro-s-triazine, wherein Y is the protein $H_3N^+—(CH_2)_4—X$. More generally, FIG. 6 shows generation of a PEG-conjugated protein with attachment of an activated PEG (e.g., the PLC 82) to an ϵ-amino group (e.g., the lysine or another amino acid such as arginine). The second chemical reaction may be implemented in an alkaline phosphate buffer (e.g., 50 mM of $K_2HPO_4$ and 105 mM of NaCl, wherein mM denotes millimoles). The second reaction can be efficiently accomplished in a wide range of media including, inter alia, saline, phosphate buffered saline, blood plasma, blood serum, albumin containing buffers, Hanks Balanced Salt Solution (HBSS), N-[2-hydroxyethyl]piperazine-N'-2-ethanesulfonic acid ("HEPES"), Roswell Park Memorial Institute 1640 ("RPMI 1640"), etc.

Time and temperature for performing the second reaction are very flexible. For example, a reaction between mPEG and amino acid of cell membranes or cell viral receptors may be accomplished in 4 minutes or longer at 4° C. if the pH is about 9. If the pH is lower (e.g., about 8), the reaction may proceed at room temperature for a longer period (e.g., 60 minutes or longer) so that the cells are not stressed by temperature and not stressed by harsh alkaline conditions. As to pH, it is useful to have a pH of about 8 when reacting mPEG with lysine. When reacting mPEG with a virus, weakly acidic to alkaline conditions should be used with a representative pH range of about 6.0 to about 9.0. When reacting mPEG with a living cell, a suitable pH range is cell specific for the particular type of living cell being reacted.

Effective doses of the PLC in the second reaction depend on several variables, including: linker chemistry, the polymer being used, surface area of cell membranes being modified, density of viral receptors, geometric factors such as available volume above the cells being modified (e.g., a higher dose may be needed to cover an upper nasal cavity than a low nasal cavity), etc.

It should be noted that the chlorine in position 6 of the cyanuric chloride triazine ring is quite unreactive and thus unavailable to react with either an amino acid or with a second polymerated linker chemical.

Figure 6:
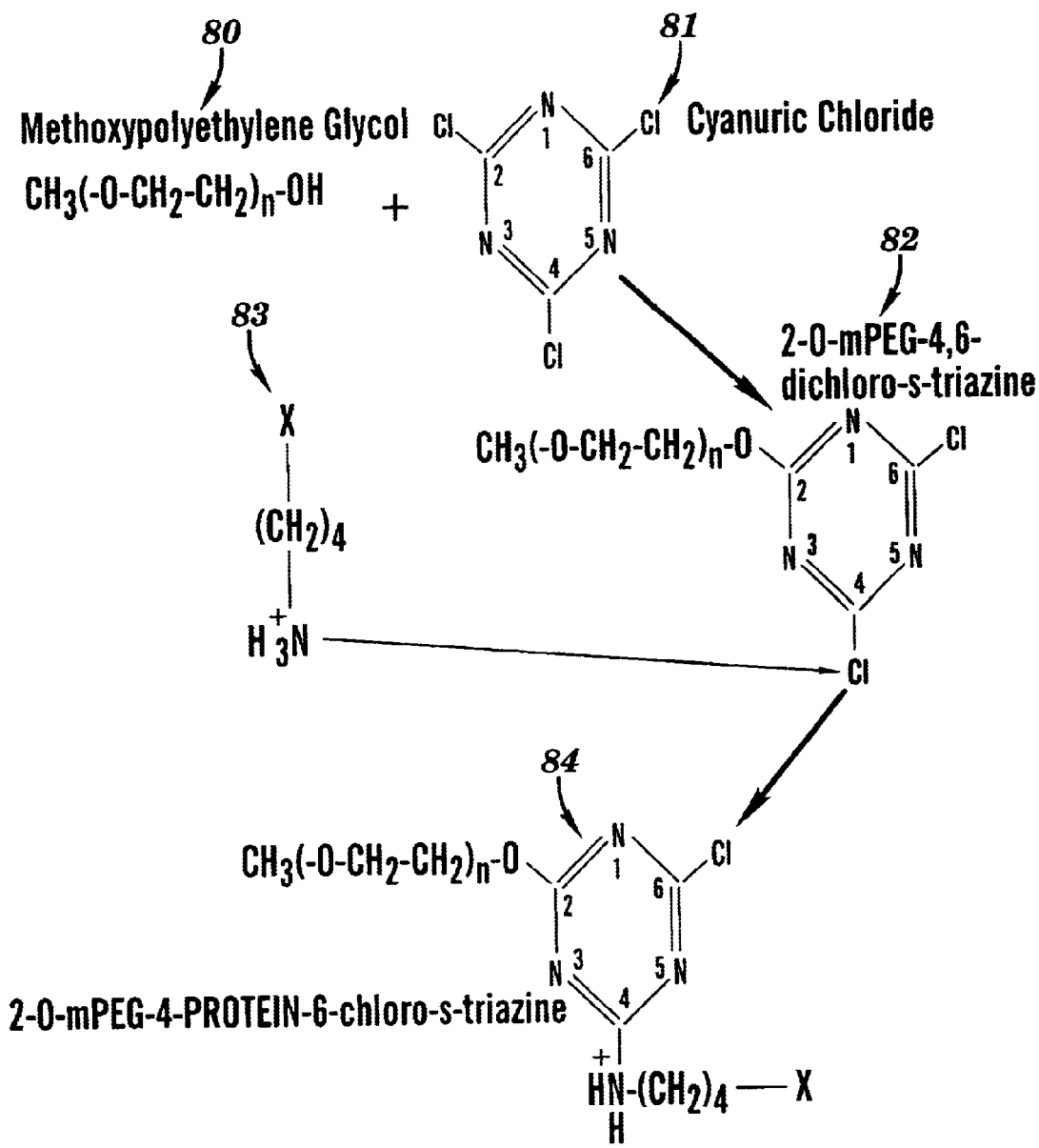
FIG. 6 depicts an exemplary chemistry of coupling the polymerated linker chemical of FIG. 2 or FIG. 3 to a protein, in accordance with embodiments of the present invention.

FIG. 6 illustrates a mechanism of the covalent attachment of the PLC of cyanuric chloride coupled mPEG with membrane proteins, and potentially membrane carbohydrates. Virtually all cells and proteins can be similarly modified (e.g., red blood cells, platelets, endothelial cells, epithelial cells, stromal cells) with only slight variations in pH, temperature and time. Indeed, the pH, time and temperature conditions at which the modification reaction can be done at are very malleable, thus making this invention applicable to a wide variety of cell types. Other polymers may be utilized instead of mPEG, such as, inter alia, polyethylene glycol, ethoxypolyethylene glycol, dextran, ficoll, and arabinogalactan. Other linker molecules may be utilized instead of cyanuric chloride, such as, inter alia, imidazolyl formate, succinimidyl succinate, succinimidyl glutarate, N-hydroxysuccinimide, 4-Nitrophenol, 2,4,5-trichlorophenol, and a chloroformate. FIG. 7 lists exemplary polymeric linker compounds (PLCs) that may be used with the present invention and associated targets that can be reacted with the PLCs. Most of the listed targets in FIG. 7 are proteins. The thiol groups in FIG. 7 include sulfhydryl groups which are protein components. Any of the PLCs that react with the hydroxyl group can be reacted with a carbohydrate. Note that the PLC of phospholipid PEG interacts with a lipid by intercalation rather than by covalent bonding.

The present invention is illustrated by the following non-limiting examples.

EXAMPLE 1

Epithelial monolayers of monkey kidney CV1 cells were covalently modified with activated mPEG (i.e., mPEG covalently bonded to a cyanuric chloride linker molecule). In particular, the cells were confluently grown on glass slides. The cells were then exposed to a solution of activated mPEG, followed by exposure to Simian Vacuolating Agent (SV40) virus for 72 hours in a medium of Minimum Essential Medium (MEM). It should be noted that the SV40 virus has veterinary significance, but does not have human significance.

Figure 8:
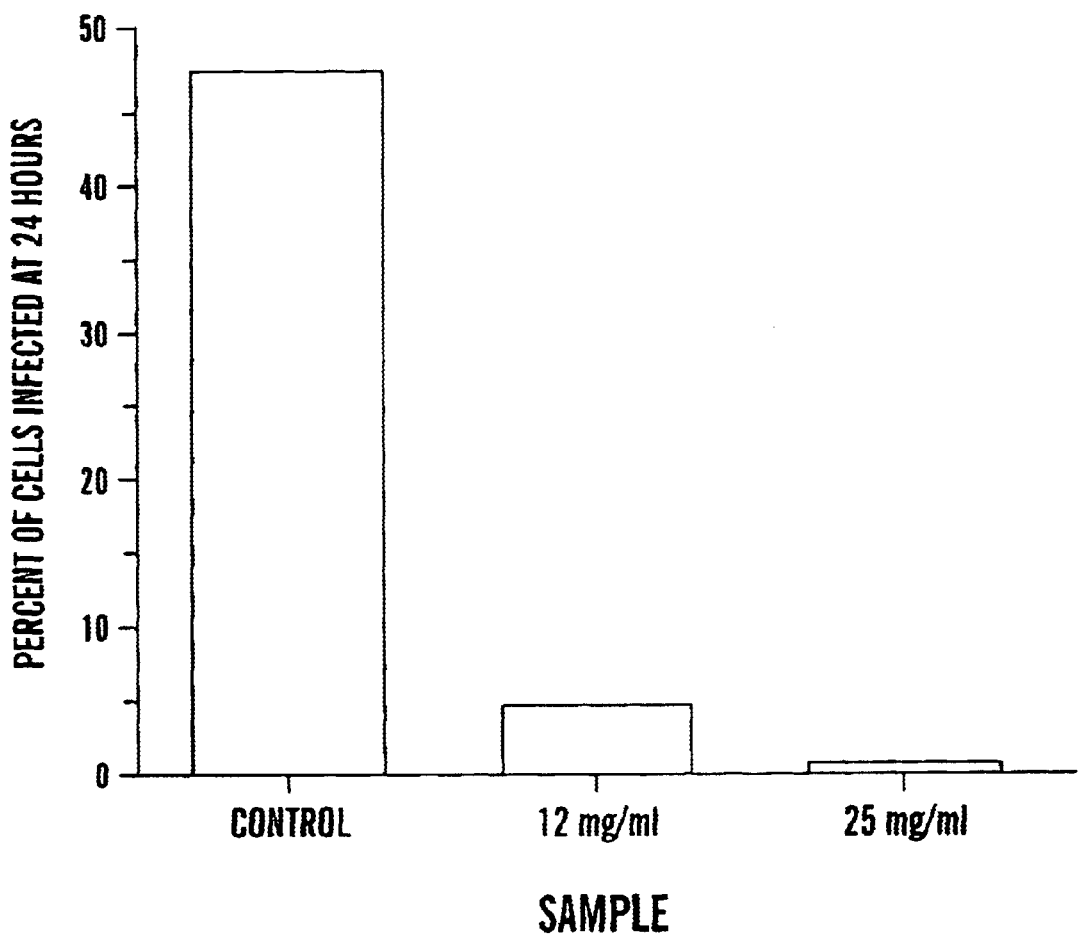
FIG. 8 is a bar graph showing the effect of covalent modification of monkey kidney epithelial cells on the rate at which the cells become infected with a virus.

FIG. 8 is a bar graph that shows the percentage of CV1 cells infected after 24 hours, as assayed via T antigen staining. Concentrations of 12 and 25 milligrams (mg) of mPEG per milliliter (ml) of medium were each analyzed. Control cells, which are not mPEG-modified, were infected at a rate of nearly 50% at 24 hours of exposure to the SV40 virus. In contrast, the 12 and 25 mg/ml samples of mPEG-modified cells were infected at a rate of only 5% and 1%, respectively, at 24 hours of exposure to the SV40 virus.

The results of this test support covalently bonding a polymerated linker chemical (e.g., activated mPEG) to membrane cell surfaces to prevent viral infection of the cells. While this test utilized mPEG as a polymer in the polymerated linker chemical, any other polymer discussed herein could have been used instead of mPEG. Similarly, while this test utilized cyanuric chloride as a linker molecule in the polymerated linker chemical, any other linker molecule discussed herein could have been used instead of cyanuric chloride. Although this test utilized monkey kidney CV1 cells, cells of other animal species (or cells of a monkey other than monkey kidney cells), could have been used instead of the monkey kidney CV1 cells.

EXAMPLE 2

SV40 virus was covalently modified with a polymerated linker chemical of activated mPEG (i.e., mPEG covalently bonded to a cyanuric chloride linker molecule) in Minimal Essential Medium (MEM) (a Cellgro® cell media product by Mediatech, Inc.), supplemented with 5% fetal bovine serum (FBS) and MEM vitamins and mineral supplement. The SV40 viruses were modified at room temperature for a period of either 30 minutes or 60 minutes. Next, epithelial monolayers of monkey kidney CV1 cells were exposed to the covalently modified SV40 virus for 72 hours in a medium of MEM.

Figure 9:
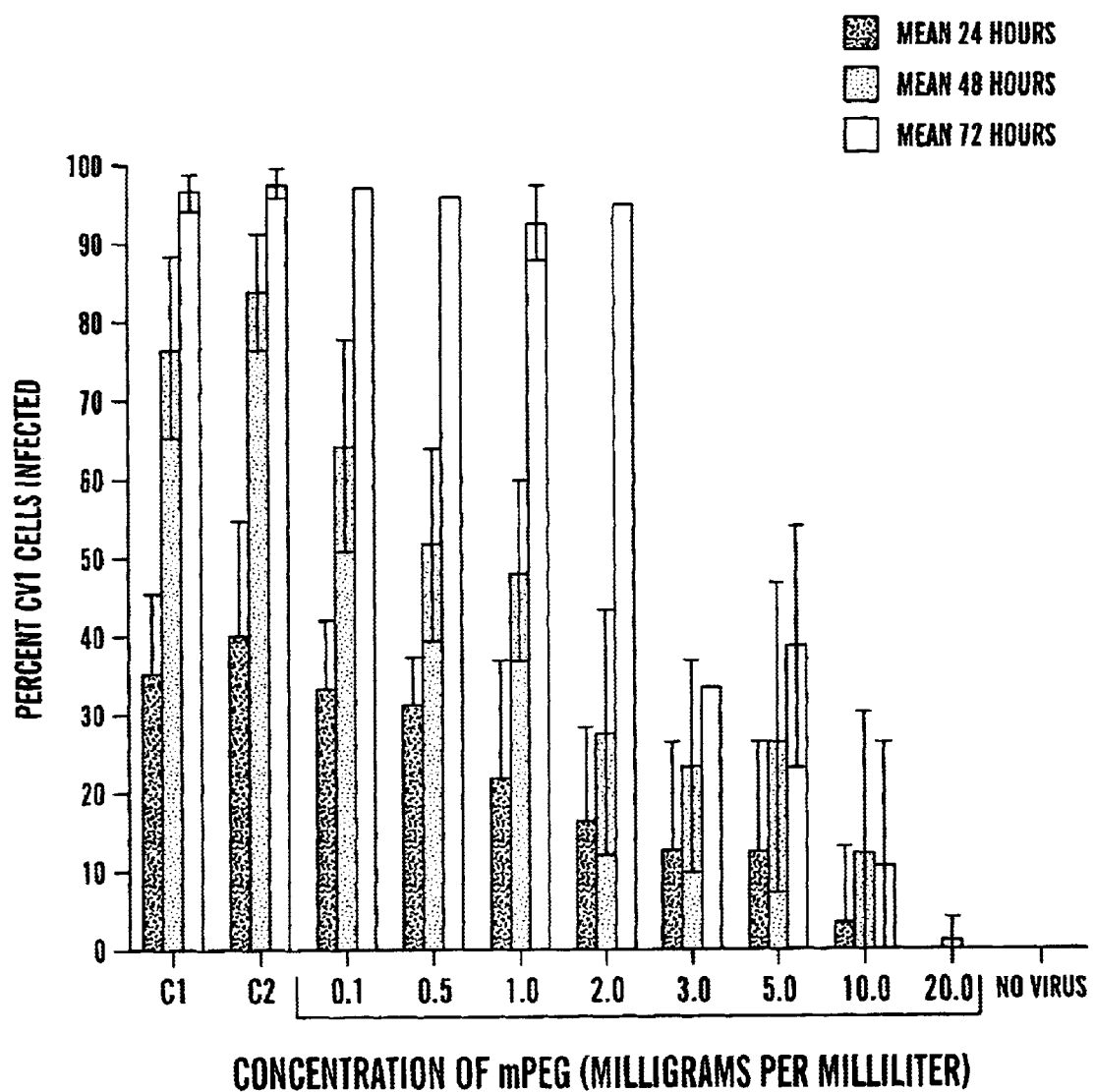
FIG. 9 is a bar graph showing the effect of covalent modification of Simian Vacuolating Agent (SV40) virus on the rate of viral infection of monkey kidney epithelial cells located near the SV40 viruses.

FIG. 9 is a bar graph that shows the percentage of CV1 cells infected after 24 hours, 48 hours, and 72 hours of SV40 virus exposure, as assayed via T antigen staining. The "I" above and below each bar denotes a standard deviation. Concentration of 0.1, 0.5, 1.0, 2.0, 3.0, 5.0, 10.0, and 20.0 mg/ml of mPEG, at a pH of 8.0, were each analyzed. C1 and C2 represent control cells not mPEG-modified, having a pH of 7.4 and 8.0 respectively. The control cells had a rate 35%–40% infection rate at 24 hours and nearly a 100% infection rate at 72 hours. The mPEG modified cells had an infection rate that decreased with concentration of mPEG. At the highest mPEG concentration of 20 milligrams/milliliter, the infection rate was only about 10% at 72 hours of SV40 virus exposure.

Figure 10:
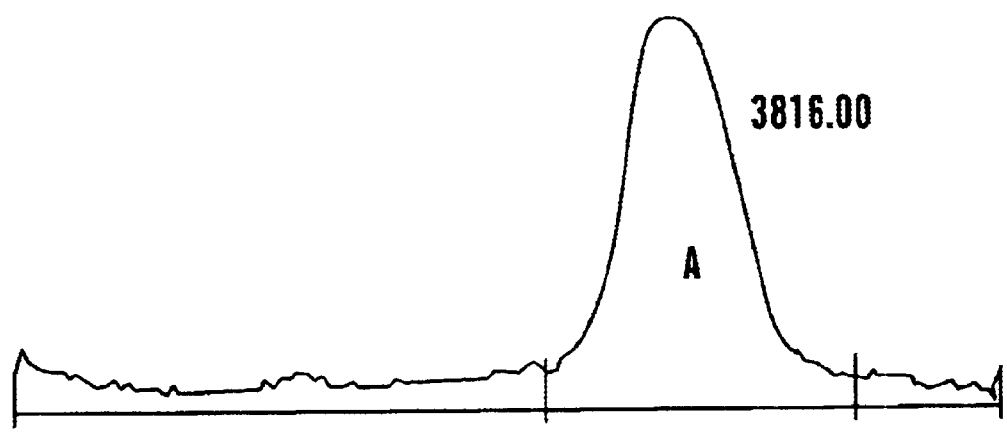
FIG. 10 depicts a densitometry curve for a control sample for the SV40 virus of FIG. 9.
Figure 11:
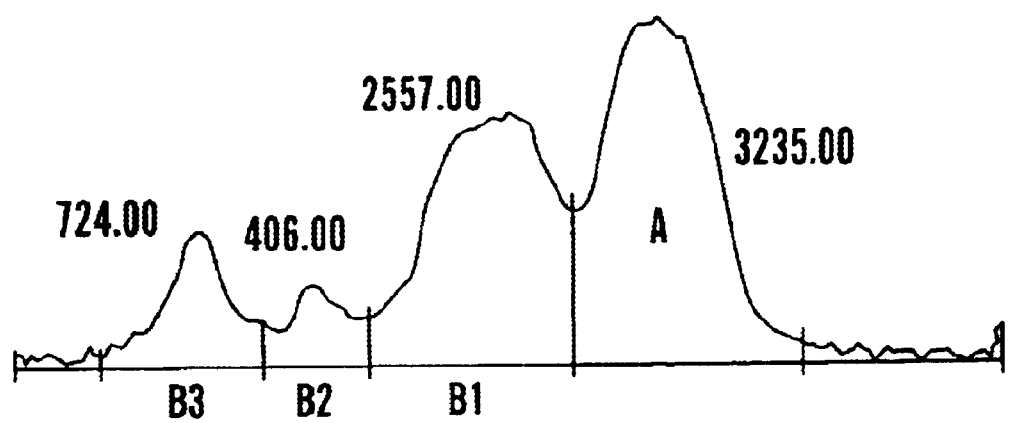
FIG. 11 depicts a densitometry curve for the covalently modified SV40 virus of FIG. 9.

FIGS. 10 and 11 depict densitometry curves, based on sodium dodecyl sulfate (SDS) polyacrylamide gel electrophoresis, that show an extent to which the SV40 virus has been covalently mPEG modified in the tests of FIG. 9. FIG. 10 depicts a densitometry curve for a control sample (C1 or C2 of FIG. 9) for the SV40 virus of FIG. 9. As stated supra, the control samples have not been mPEG modified. The "A" portion of the densitometry curve of FIG. 10 represents a VP1 protein of the SV40 viral capsid, as detected by an anti-VP1 antibody. The indicated value of 3816 represents the area under the curve of the "A" portion that denotes the VP1 antibody response and serves as a reference value for subsequent comparison purposes.

FIG. 11 depicts a densitometry curve for the covalently mPEG-modified SV40 virus of FIG. 9. The "A" portion of the densitometry curve of FIG. 11 represents a VP1 protein of the SV40 viral capsid and the indicated area of 3235 represents a small decrease in VP1 antibody response". The "B1", "B2", and "B3" portions of the densitometry curve of FIG. 11 respectively represents an antibody response to 1 mPEG, 2 mPEGs, and 3 mPEGs, covalently bonded to a single protein. The indicated values of 2557, 406, and 724 for the areas under the B1, B2, and B3 curves, respectively, denote relative abundances of the 1 mPEG-modified proteins, 2 mPEG-modified proteins, and 3 mPEG-modified proteins. The presence of the B1, B2, and B3 portions of the densitometry curve of FIG. 11, and the absence of B1, B2, and B3 portions in the control sample of FIG. 10, demonstrates that covalent bonding of the SV40 virus with activated mPEG indeed occurred for the tests of FIG. 9.

The results of this test support covalently bonding a polymerated linker chemical (e.g., activated mPEG) to a virus so as to inactivate an ability of the virus to infect adjacent or nearby cells of an animal. While this test utilized mPEG as a polymer in the polymerated linker chemical, any other polymer discussed herein could have been used instead of mPEG. Similarly, while this test utilized cyanuric chloride as a linker molecule in the polymerated linker chemical, any other linker molecule discussed herein could have been used instead of cyanuric chloride. Although this test utilized monkey kidney CV1 cells, cells of other animal species (or cells of a monkey other than monkey kidney cells), could have been used instead of the monkey kidney CV1 cells.

While particular embodiments of the present invention have been described herein for purposes of illustration, many modifications and changes will become apparent to those skilled in the art. Accordingly, the appended claims are intended to encompass all such modifications and changes as fall within the true spirit and scope of this invention.

What is claimed is:

1. A chemo-physiological structure, comprising:
a cell of an animal, said cell having a membrane surface;
a viral receptor coupled to the membrane surface; and
a linker molecule covalently bonded to a tissue member selected from the group consisting of the membrane surface, the viral receptor, and a combination thereof, wherein a polymer is covalently attached to the linker molecule, and wherein the polymer prevents an extracellular virus from bonding to the viral receptor.

2. A chemo-physiological structure, comprising:
a cell of an animal, said cell having a membrane surface;
a viral receptor coupled to the membrane surface; and
a linker molecule covalently bonded to the membrane surface, wherein a polymer is covalently attached to the linker molecule, and wherein the polymer prevents an extracellular virus from bonding to the viral receptor.

3. The chemo-physiological structure of claim 2, further comprising the extracellular virus, wherein the linker molecule together with the covalently attached polymer is disposed between the virus and the viral receptor.

4. The chemo-physiological structure of claim 2, wherein the polymer is selected from the group consisting of polyethylene glycol, methoxypolyethylene glycol, ethoxypolyethylene glycol, dextran, ficoll, and arabinogalactan.

5. The chemo-physiological structure of claim 2, wherein the linker molecule is selected from the group consisting of cyanuric chloride, imidazolyl formate, succinimidyl succinate, succinimidyl glutarate, N-hydroxysuccinimide, 4-Nitrophenol, 2,4,5-trichlorophenol, and a chloroformate.

6. The chemo-physiological structure of claim 2, further comprising the extracellular virus, wherein the virus is capable of infecting cells of a human animal.

7. The chemo-physiological structure of claim 2, further comprising the extracellular virus, wherein the virus is capable of infecting cells of a non-human animal.

8. The chemo-physiological structure of claim 2, wherein the linker molecule is covalently bonded to an amino acid at the membrane surface.

9. The chemo-physiological structure of claim 2, wherein the linker molecule is covalently bonded to a lysine group at the membrane surface.

10. The chemo-physiological structure of claim 2, wherein the linker molecule is covalently bonded to a carbohydrate at the membrane surface.

11. The chemo-physiological structure of claim 2, wherein the linker molecule is covalently bonded to a sulfhydryl group at the membrane surface.

12. A chemo-physiological structure, comprising:
a cell of an animal, said cell having a membrane surface;
a viral receptor coupled to the membrane surface; and
a linker molecule covalently bonded to the viral receptor, wherein a polymer is covalently attached to the linker molecule, and wherein the polymer prevents an extracellular virus from bonding to the viral receptor.

13. The chemo-physiological structure of claim 12, further comprising the extracellular virus, wherein the linker molecule together with the covalently attached polymer is disposed between the virus and the viral receptor.

14. The chemo-physiological structure of claim 12, wherein the polymer is selected from the group consisting of polyethylene glycol, methoxypolyethylene glycol, ethoxypolyethylene glycol, dextran, ficoll, and arabinogalactan.

15. The chemo-physiological structure of claim 12, wherein the linker molecule is selected from the group consisting of cyanuric chloride, imidazolyl formate, succinimidyl succinate, succinimidyl glutarate, N-hydroxysuccinimide, 4-Nitrophenol, 2,4,5-trichlorophenol, and a chloroformate.

16. The chemo-physiological structure of claim 12, further comprising the extracellular virus, wherein the virus is capable of infecting cells of a human animal.

17. The chemo-physiological structure of claim 12, further comprising the extracellular virus, wherein the virus is capable of infecting cells of a non-human animal.

18. The chemo-physiological structure of claim 12, wherein the linker molecule is covalently bonded to an amino acid at the viral receptor.

19. The chemo-physiological structure of claim 12, wherein the linker molecule is covalently bonded to a lysine group at the viral receptor.

20. The chemo-physiological structure of claim 12, wherein the linker molecule is covalently bonded to a carbohydrate at the viral receptor.

21. The chemo-physiological structure of claim 12, wherein the tinker molecule is covalently bonded to a sulfhydryl group at the viral receptor.

22. A chemo-physiological structure, comprising:
a cell of an animal, said cell having a membrane surface, said cell selected from the group consisting of an epithelial cell and an endothelial cell;
a viral receptor coupled to the membrane surface; and
a linker molecule covalently bonded to a tissue member selected from the group consisting of the membrane surface, the viral receptor, and a combination thereof, wherein a polymer is covalently attached to the linker molecule, and wherein the polymer prevents an extracellular virus from bonding to the viral receptor.

23. The chemo-physiological structure of claim 22, wherein the cell consists of the epithelial cell, and wherein the tissue member consists of the membrane surface.

24. The chemo-physiological structure of claim 22, wherein the virus is capable of infecting cells of a human animal, wherein the cell consists of the epithelial cell, and wherein the tissue member consists of the membrane surface.

25. The chemo-physiological structure of claim 22, wherein the cell consists of the epithelial cell, and wherein the tissue member consists of the viral receptor.

26. The chemo-physiological structure of claim 22, wherein the virus is capable of infecting cells of a human animal, wherein the cell consists of the epithelial cell, and wherein the tissue member consists of the viral receptor.

27. The chemo-physiological structure of claim 22, wherein the cell consists of the endothelial cell, and wherein the tissue member consists of the membrane surface.

28. The chemo-physiological structure of claim 22, wherein the virus is capable of infecting cells of a human animal, wherein the cell consists of the endothelial cell, and wherein the tissue member consists of the membrane surface.

29. The chemo-physiological structure of claim 22, wherein the cell consists of the epithelial cell, and wherein the tissue member consists of the viral receptor.

30. The chemo-physiological structure of claim 22, wherein the cell consists of the endothelial cell, and wherein the tissue member consists of the viral receptor.

31. A chemo-physiological structure, comprising:
a nasal epithelial cell of an animal, said nasal epithelial cell having a membrane surface;
a viral receptor coupled to the membrane surface; and
a linker molecule covalently bonded to a tissue member selected from the group consisting of the membrane surface, the viral receptor, and a combination thereof, wherein a polymer is covalently attached to the linker molecule, and wherein the polymer prevents an extracellular virus from bonding to the viral receptor.

32. The chemo-physiological structure of claim 31, wherein the tissue member consists of the membrane surface.

33. The chemo-physiological structure of claim 32, further comprising the extracellular virus, wherein the linker molecule together with the covalently attached polymer is disposed between the virus and the viral receptor.

34. The chemo-physiological structure of claim 32, wherein the polymer is selected from the group consisting of polyethylene glycol, methoxypolyethylene glycol, ethoxypolyethylene glycol, dextran, ficoll, and arabinogalactan.

35. The chemo-physiological structure of claim 32, wherein the linker molecule is selected from the group consisting of cyanuric chloride, imidazolyl formate, succinimidyl succinate, succinimidyl glutarate, N-hydroxysuccinimide, 4-Nitrophenol, 2,4,5-trichlorophenol, and a chloroformate.

36. The chemo-physiological structure of claim 32, further comprising the extracellular virus, wherein the virus is capable of infecting cells of a human animal.

37. The chemo-physiological structure of claim 32, further comprising the extracellular virus, wherein the virus is capable of infecting cells of a non-human animal.

38. The chemo-physiological structure of claim 32, wherein the linker molecule is covalently bonded to an amino acid at the membrane surface.

39. The chemo-physiological structure of claim 32, wherein the linker molecule is covalently bonded to a lysine group at the membrane surface.

40. The chemo-physiological structure of claim 32, wherein the linker molecule is covalently bonded to a carbohydrate at the membrane surface.

41. The chemo-physiological structure of claim 32, wherein the linker molecule is covalently bonded to a sulfhydryl group at the membrane surface.

42. The chemo-physiological structure of claim 31, wherein the tissue member consists of the viral receptor.

43. The chemo-physiological structure of claim 42, further comprising the extracellular virus, wherein the linker molecule together with the covalently attached polymer is disposed between the virus and the viral receptor.

44. The chemo-physiological structure of claim 42 wherein the polymer is selected from the group consisting of polyethylene glycol, methoxypolyethylene glycol, ethoxypolyethylene glycol, dextran, ficoll, and arabinogalactan.

45. The chemo-physiological structure of claim 42, wherein the linker molecule is selected from the group consisting of cyanuric chloride, imidazolyl formate, succinimidyl succinate, succinimidyl glutarate, N-hydroxysuccinimide, 4-Nitrophenol, 2,4,5-trichlorophenol, and a chloroformate.

46. The chemo-physiological structure of claim 42, further comprising the extracellular virus, wherein the virus is capable of infecting cells of a human animal.

47. The chemo-physiological structure of claim 42, further comprising the extracellular virus, wherein the virus is capable of infecting cells of a non-human animal.

48. The chemo-physiological structure of claim 42, wherein the linker molecule is covalently bonded to an amino acid at the membrane surface.

49. The chemo-physiological structure of claim 42, wherein the linker molecule is covalently bonded to a lysine group at the membrane surface.

50. The chemo-physiological structure of claim 42, wherein the linker molecule is covalently bonded to a carbohydrate at the membrane surface.

51. The chemo-physiological structure of claim 42, wherein the linker molecule is covalently bonded to a sulfhydryl group at the membrane surface.

52. A chemo-physiological structure, comprising:

a pulmonary cell of an animal, said pulmonary cell having a membrane surface;

a viral receptor coupled to the membrane surface; and a linker molecule covalently bonded to a tissue member selected from the group consisting of the membrane surface, the viral receptor, and a combination thereof, wherein a polymer is covalently attached to the linker molecule, and wherein the polymer prevents an extracellular virus from bonding to the viral receptor.

53. The chemo-physiological structure of claim 52, wherein the tissue member consists of the membrane surface.

54. The chemo-physiological structure of claim 52, wherein the tissue member consists of the viral receptor.

55. A chemo-physiological structure, comprising:

a vaginal cell of an animal, said vaginal cell having a membrane surface;

a viral receptor coupled to the membrane surface; and a linker molecule covalently bonded to a tissue member selected from the group consisting of the membrane surface, the viral receptor, and a combination thereof, wherein a polymer is covalently attached to the linker molecule, and wherein the polymer prevents an extracellular virus from bonding to the viral receptor.

56. The chemo-physiological structure of claim 55, wherein the tissue member consists of the membrane surface.

57. The chemo-physiological structure of claim 55, wherein the tissue member consists of the viral receptor.

58. A chemo-physiological structure, comprising:

a cell of an animal, said cell having a membrane surface;

a viral receptor coupled to the membrane surface; and a linker molecule covalently bonded to a tissue member selected from the group consisting of the membrane surface, the viral receptor, and a combination thereof, wherein a polymer is covalently attached to the linker molecule, and wherein the polymer has a long chain length that prevents an extracellular virus from bonding to the viral receptor.

59. A chemo-physiological structure, comprising:
a cell of an animal, said cell having a membrane surface;
a viral receptor coupled to the membrane surface; and
a linker molecule covalently bonded to a tissue member selected from the group consisting of the membrane surface, the viral receptor, and a combination thereof, wherein a polymer is covalently attached to the linker molecule, and wherein the polymer inactivates a charge-charge interaction that would otherwise bind an extracellular virus to the viral receptor.

60. A chemo-physiological structure, comprising:
a cell of an animal, said cell having a membrane surface;
a viral receptor coupled to the membrane surface; and
a linker molecule covalently bonded to a tissue member selected from the group consisting of the membrane surface, the viral receptor, and a combination thereof, wherein a polymer is covalently attached to the linker molecule, and wherein the polymer prevents an extracellular virus from entering an interior portion of the cell.

61. A method for forming a chemo-physiological structure, comprising:
providing a cell of an animal, wherein a viral receptor is coupled to a membrane surface of the cell; and
covalently bonding a linker molecule to a tissue member selected from the group consisting of the membrane surface, the viral receptor, and a combination thereof, wherein a polymer is covalently attached to the linker molecule, and wherein the polymer prevents an extracellular virus from bonding to the viral receptor.

62. The method of claim 61, further comprising providing the extracellular virus, wherein the linker molecule together with the covalently attached polymer is disposed between the virus and the viral receptor.

63. The method of claim 61, wherein the polymer is selected from the group consisting of polyethylene glycol, methoxypolyethylene glycol, ethoxypolyethylene glycol, dextran, ficoll, and arabinogalactan.

64. The method of claim 61, wherein the linker molecule is selected from the group consisting of cyanuric chloride, imidazolyl formate, succinimidyl succinate, succinimidyl glutarate, N-hydroxysuccinimide, 4-Nitrophenol, 2,4,5-trichlorophenol, and a chloroformate.

65. The method of claim 61, further comprising providing the extracellular virus, wherein the virus is capable of infecting cells of a human animal.

66. The method of claim 61, further comprising providing the extracellular virus, wherein the virus is capable of infecting cells of a non-human animal.

67. The method of claim 61, wherein covalently bonding the linker molecule to the member includes covalently bonding the linker molecule to an amino acid at the tissue member.

68. The method of claim 61, wherein covalently bonding the linker molecule to the tissue member includes covalently bonding the linker molecule to a lysine group at the tissue member.

69. The method of claim 61, wherein covalently bonding the linker molecule to the tissue member includes covalently bonding the linker molecule to a carbohydrate at the tissue member.

70. The method of claim 61, wherein covalently bonding the linker molecule to the tissue member includes covalently bonding the linker molecule to a sulhydryl group at the tissue member.

71. A method for forming a chemo-physiological structure, comprising:
providing a cell of an animal, wherein a viral receptor is coupled to a membrane surface of the cell; and
covalently bonding a linker molecule bonded to the membrane surface, wherein a polymer is covalently attached to the linker molecule, and wherein the polymer prevents an extracellular virus from bonding to the viral receptor.

72. The method of claim 71, further comprising providing the extracellular virus, wherein the linker molecule together with the covalently attached polymer is disposed between the virus and the viral receptor.

73. The method of claim 71, wherein the polymer is selected from the group consisting of polyethylene glycol, methoxypolyethylene glycol, ethoxypolyethylene glycol, dextran, ficoll, and arabinogalactan.

74. The method of claim 71, wherein the linker molecule is selected from the group consisting of cyanuric chloride, imidazolyl formate, succinimidyl succinate, succinimidyl glutarate, N-hydroxysuccinimide, 4-Nitrophenol, 2,4,5-trichlorophenol, and a chloroformate.

75. The method of claim 71, further comprising providing the extracellular virus, wherein the virus is capable of infecting cells a human animal.

76. The method of claim 71, further comprising providing the extracellular virus, wherein the virus is capable of infecting cells of a non-human animal.

77. The method of claim 71, wherein covalently bonding the linker molecule to the membrane surface includes covalently bonding the linker molecule to an amino acid at the membrane surface.

78. The method of claim 71, wherein covalently bonding the linker molecule to the membrane surface includes covalently bonding the linker molecule to a lysine group at the membrane surface.

79. The method of claim 71, wherein covalently bonding the linker molecule to the membrane surface includes covalently bonding the linker molecule to a carbohydrate at the membrane surface.

80. The method of claim 71, wherein covalently bonding the linker molecule to the membrane surface includes covalently bonding the linker molecule to a sulfhydryl group at the membrane surface.

81. A method for forming a chemo-physiological structure, comprising:
providing a cell of an animal, wherein a viral receptor is coupled to a membrane surface of the cell; and
covalently bonding a linker molecule bonded to the viral receptor, wherein a polymer is covalently attached to the linker molecule, and wherein the polymer prevents an extracellular virus from bonding to the viral receptor.

82. The method of claim 81, further comprising providing the extracellular virus, wherein the linker molecule together with the covalently attached polymer is disposed between the virus and the viral receptor.

83. The method of claim 81, wherein the polymer is selected from the group consisting of polyethylene glycol, methoxypolyethylene glycol, ethoxypolyethylene glycol, dextran, ficoll, and arabinogalactan.

84. The method of claim 81, wherein the linker molecule is selected from the group consisting of cyanuric chloride, imidazolyl formate, succinimidyl succinate, succinimidyl glutarate, N-hydroxysuccinimide, 4-Nitrophenol, 2,4,5-trichlorophenol, and a chloroformate.

85. The method of claim 81, further comprising providing the extracellular virus, wherein the virus is capable of infecting cells of a human animal.

86. The method of claim 81, further comprising providing the extracellular virus, wherein the virus is capable of infecting cells of a non-human animal.

87. The method of claim 81, wherein covalently bonding the linker molecule to the viral receptor includes covalently bonding the linker molecule to an amino acid at the viral receptor.

88. The method of claim 81, wherein covalently bonding the linker molecule to the viral receptor includes covalently bonding the linker molecule to a lysine group at the viral receptor.

89. The method of claim 81, wherein covalently bonding the linker molecule to the viral receptor includes covalently bonding the linker molecule to a carbohydrate at the viral receptor.

90. The method of claim 81, wherein covalently bonding the linker molecule to the viral receptor includes covalently bonding the linker molecule to a sulfhydryl group at the viral receptor.

91. A method for forming a chemo-physiological structure, comprising:
providing a cell of an animal, wherein a viral receptor is coupled to a membrane surface of the cell, said cell selected from the group consisting of an endothelial cell and an epithelial cell; and
covalently bonding a linker molecule to a tissue member selected from the group consisting of the membrane surface, the viral receptor, and a combination thereof, wherein a polymer is covalently attached to the linker molecule, and wherein the polymer prevents an extracellular virus from bonding to the viral receptor.

92. The method of claim 91, wherein the cell consists of the epithelial cell, and wherein the tissue member consists of the membrane surface.

93. The method of claim 91, wherein the cell consists of the epithelial cell, and wherein the tissue member consists of the viral receptor.

94. The method of claim 91, wherein the cell consists of the endothelial cell, and wherein the tissue member consists of the membrane surface.

95. The method of claim 91, wherein the cell consists of the endothelial cell, and wherein the tissue member consists of the viral receptor.

96. A method for forming a chemo-physiological structure, comprising:
providing a nasal epithelial cell of an animal, wherein a viral receptor is coupled to a membrane surface of the nasal epithelial cell; and
covalently bonding a linker molecule to a tissue member selected from the group consisting of the membrane surface, the viral receptor, and a combination thereof, wherein a polymer is covalently attached to the linker molecule, and wherein the polymer prevents an extracellular virus from bonding to the viral receptor.

97. The method of claim 96, wherein the tissue member consists of the membrane surface.

98. The method of claim 97, further comprising providing the extracellular virus, wherein the linker molecule together with the covalently attached polymer is disposed between the virus and the viral receptor.

99. The method of claim 97, wherein the polymer is selected from the group consisting of polyethylene glycol, methoxypolyethylene glycol, ethoxypolyethylene glycol, dextran, ficoll, and arabinogalactan.

100. The method of claim 97, wherein the linker molecule is selected from the group consisting of cyanuric chloride, imidazolyl formate, succinimidyl succinate, succinimidyl glutarate, N-hydroxysuccinimide, 4-Nitrophenol, 2,4,5-trichlorophenol, and a chloroformate.

101. The method of claim 97, further comprising providing the extracellular virus, wherein the virus is capable of infecting cells of a human animal.

102. The method of claim 97, further comprising providing the extracellular virus, wherein the virus is capable of infecting cells of a non-human animal.

103. The method of claim 97, wherein covalently bonding the linker molecule to the membrane surface includes covalently bonding the linker molecule to an amino acid at the membrane surface.

104. The method of claim 97, wherein covalently bonding the linker molecule to the membrane surface includes covalently bonding the linker molecule to a lysine group at the membrane surface.

105. The method of claim 97, wherein covalently bonding the linker molecule to the membrane surface includes covalently bonding the linker molecule to a carbohydrate at the membrane surface.

106. The method of claim 97, wherein covalently bonding the linker molecule to the membrane surface includes covalently bonding the linker molecule to a sulfhydryl group at the membrane surface.

107. The method of claim 96, wherein the tissue member consists of the viral receptor.

108. The method of claim 107, further comprising providing the extracellular virus, wherein the linker molecule together with the covalently attached polymer is disposed between the virus and the viral receptor.

109. The method of claim 107, wherein the polymer is selected from the group consisting of polyethylene glycol, methoxypolyethylene glycol, ethoxypolyethylene glycol, dextran, ficoll, and arabinogalactan.

110. The method of claim 107, wherein the linker molecule is selected from the group consisting of cyanuric chloride, imidazolyl formate, succinimidyl succinate, succinimidyl glutarate, N-hydroxysuccinimide, 4-Nitrophenol, 2,4,5-trichlorophenol, and a chloroformate.

111. The method of claim 107, further comprising providing the extracellular virus, wherein the virus in capable of infecting cells of a human animal.

112. The method of claim 107, further comprising providing the extracellular virus, wherein the virus is capable of infecting cells of a non-human animal.

113. The method of claim 107, wherein covalently bonding the linker molecule to the viral receptor includes covalently bonding the linker molecule to an amino acid at the viral receptor.

114. The method of claim 107, wherein covalently bonding the linker molecule to the viral receptor includes covalently bonding the linker molecule to a lysine group at the viral receptor.

115. The method of claim 107, wherein covalently bonding the linker molecule to the viral receptor includes covalently bonding the linker molecule to a carbohydrate at the viral receptor.

116. The method of claim 107, wherein covalently bonding the linker molecule to the viral receptor includes covalently bonding the linker molecule to a sulfhydryl group at the viral receptor.

117. A method for forming a chemo-physiological structure, comprising providing a pulmonary cell of an animal, wherein a viral receptor is coupled to a membrane surface of the pulmonary cell; and covalently bonding a linker molecule to a tissue member selected from the group consisting of the membrane surface, the viral receptor, and a combination thereof, wherein a polymer is covalently attached to the linker molecule, and wherein the polymer prevents an extracellular virus from bonding to the viral receptor.

118. The method of claim 117, wherein the tissue member consists of the membrane surface.

119. The method of claim 117, wherein the tissue member consists of the viral receptor 120. A method for forming a chemo-physiological structure, comprising:

providing a vaginal cell of an animal, wherein a viral receptor coupled to the membrane surface of the vaginal cell; and covalently bonding a linker molecule to a tissue member selected from the group consisting of the membrane surface, the viral receptor, and a combination thereof, wherein a polymer is covalently attached to the linker molecule, and wherein the polymer prevents an extracellular virus from bonding to the viral receptor.

121. The method of claim 120, wherein the tissue member consists of the membrane surface.

122. The method of claim 120, wherein the tissue member consists of the viral receptor.

123. A method for forming a chemo-physiological structure, comprising:

providing a cell of an animal, wherein the cell has a membrane surface, and wherein a viral receptor is coupled to the membrane surface; and covalently bonding a linker molecule to a tissue member selected from the group consisting of the membrane surface, the viral receptor, and a combination thereof, wherein a polymer is covalently attached to the linker molecule, and wherein the polymer has a long chain length that prevents an extracellular virus from bonding to the viral receptor.

124. A method for forming a chemo-physiological structure, comprising:

providing a cell of an animal, wherein the cell has a membrane surface, and wherein a viral receptor is coupled to the membrane surface; and covalently bonding a linker molecule to a tissue member selected from the group consisting of the membrane surface, the viral receptor, and a combination thereof, wherein a polymer inactivates a charge-charge interaction that would otherwise bind an extracellular virus to the viral receptor.

125. A method for forming a chemo-physiological structure, comprising:

providing a cell of an animal, wherein the cell has a membrane surface, and wherein a viral receptor is coupled to the membrane surface; and covalently bonding a linker molecule to a tissue member selected from the group consisting of the membrane surface, the viral receptor, and a combination thereof, wherein a polymer is covalently attached to the linker molecule, and wherein the polymer prevents an extracellular virus from entering an interior portion of the cell.

* * * * *

UNITED STATES PATENT AND TRADEMARK OFFICE
CERTIFICATE OF CORRECTION

PATENT NO. : 6,699,465 B2
APPLICATION NO. : 09/861491
DATED : March 2, 2004
INVENTOR(S) : Mark D. Scott Page 1 of 1

It is certified that error appears in the above-identified patent and that said Letters Patent is hereby corrected as shown below:

<u>Column 14,</u>
Line 3, delete "sulhydryl" and insert -- sulfhydryl --.

Signed and Sealed this

Twenty-seventh Day of June, 2006

JON W. DUDAS
*Director of the United States Patent and Trademark Office*